United States Patent
Weinstein (12)

(10) Patent No.: US 6,569,423 B2
(45) Date of Patent: May 27, 2003

(54) METHODS OF INDUCING NERVOUS TISSUE REGENERATION

(75) Inventor: David E. Weinstein, Dobbs Ferry, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 19 days.

(21) Appl. No.: 09/294,764

(22) Filed: Apr. 19, 1999

(65) Prior Publication Data

US 2002/0146395 A1 Oct. 10, 2002

(51) Int. Cl.$^7$ .......................... C12N 5/00; C12N 15/63; A01N 63/00
(52) U.S. Cl. ................... 424/93.21; 424/93.2; 435/325; 435/455; 435/373
(58) Field of Search ............................ 424/93.2, 93.21; 514/44; 435/373, 325, 455

(56) References Cited

PUBLICATIONS

Rudinger et al., Characteristics of the amino acids as components of a peptide hormone sequence, 1976, Peptide Hormones, pp. 1–7.*

Kaye et al., A singel amino acid substitution results in retinoblastoma protein defective in a phosphorylation and oncoprotein binding, Sep. 1990, Proc. Natl. Acad. Sci., vol. 87, pp. 6922–6926.*

Lanza et al., Molecular Medicine Today, p. 39–45, Jan. 1998.*

Hammer C., Pathologie Biologie, p. 203–207, Mar. 1994.*

David E. Weinstein et al., *Molec. and Cell. Neurosc.*, 6:212–229, 1995.

Phyllis L. Bieri et al., *J. Neurosc. Res.*, 50:821–828, 1997.

Majorie Gondré et al., *J. Cell Biol.*, 141 (2) 493–501, Apr. 1998.

* cited by examiner

*Primary Examiner*—Shin-Lin Chen
(74) *Attorney, Agent, or Firm*—Amster, Rothstein & Ebenstein

(57) ABSTRACT

This invention relates to a method of regenerating nervous tissue by contacting the tissue with Schwann cells that express ΔSCIP. The inventors have demonstrated herein that Schwann cells expressing ΔSCIP induce regeneration of nervous tissue. Also provided by the present invention is a method for treating a subject in need of nervous tissue regeneration by introducing Schwann cells expressing ΔSCIP into the subject.

1 Claim, 9 Drawing Sheets

METHODS OF INDUCING NERVOUS TISSUE REGENERATION

BACKGROUND OF THE INVENTION

Regeneration is a hallmark of the peripheral nervous system (PNS) such that PNS axons are capable of both finding their original target tissues and re-establishing functional synapses with a high degree of fidelity. Following compression injury, peripheral nerves undergo a stereotyped pattern of Wallerian degeneration, characterized by myelin decompaction and phagocytosis as well as axonal die-back, which leaves intact endotubes formed by the residual basal lamina and the associated Schwann cells (reviewed in Griffin et al., 1996). The endotubes form channels into which the regenerated axons will grow. Before degeneration is complete the PNS begins the process of regeneration, which will result in complete recovery. At the onset of axonal regeneration the proximal nerve stumps form new sprouts which re-enter the endo-tubes (Bray et al., 1972; McQuarrie, 1985), and grow toward their targets. Although the basal lamina is necessary for regeneration, it is not sufficient (Hall, 1986; Ide et al., 1983). Several groups have demonstrated that Schwann cells are associated with and are required for regenerating axons to re-enter the distal stump. This is the case whether the fibers are growing into heterologous basal lamina (Feneley et al., 1991), a cellular nerve grafts (Gulati, 1988), or are sprouting into distal nerves after degeneration (Fawcett and Keynes, 1988). In addition, axons fail to regenerate across physical gaps in the absence of Schwann cells (Jenq et al., 1988; Le Beau et al., 1988; Scaravilli et al., 1986). Taken together, these data suggest that viable Schwann cells are required for axonal extension after injury, even in the permissive micro-environment of the basal lamina into which axons readily elongate.

The inventors have been interested in the transcriptional regulation of PNS development and regeneration. The transcription factor SCIP (also known as Oct-6 and Tst-1 (He, 1991; Suzuki et al., 1990)), a member of the POU family of transcription factors, is expressed in both developing and regenerating Schwann cells. SCIP is known to regulate the myelin structural genes $P_0$ and MBP when it is expressed by Schwann cells during a narrow window of development termed promyelination (Monuki et al., 1993; Weinstein et al., 1995). In the adult, SCIP expression is undetectable in the Schwann cell unless the nerve is injured, after which the gene is re-expressed as axons enter the distal nerve stump (Zorick, 1996). The inventors have been interested in the function of SCIP during PNS development and have recently reported on the generation of transgenic mice which express a mutant form of SCIP, termed ΔSCIP (Weinstein et al., 1995). The transgene is under the transcriptional control of the $P_0$ promoter, which the inventors and others have used to target expression uniquely to the Schwann cell (Lemke et al., 1988; Messing et al., 1992; Messing et al., 1994). The lines of mice the inventors have isolated and described are single copy gene transgenics which express the ΔSCIP transgene in a Schwann cell-specific manner (Weinstein et al., 1995). The mutant SCIP protein has a deleted amino terminus, but an intact POU domain, which allows for DNA binding and POU-specific domain protein-protein interactions (Fyodorov and Deneris, 1996; Weinstein et al., 1995). Data from the study of animals that are SCIP-null suggest that SCIP function is required for the entry into and maintenance of the promyelinating phase of development (Bermingham et al., 1996; Jaegle et al., 1996; Weinstein et al., 1995). Schwann cells from animals that are null at the SCIP locus stall in their differentiation program at the onset of promyelination (Jaegle et al., 1996), and the ΔSCIP animals which express an $NH_2$ terminal deleted gene in mid-promyelination precociously exit this phase and enter into myelination. This early phenotypic switch results in an alteration in the 1:1 association of myelinating Schwann cells and their axons as well as an overexpression of the myelin structural genes. Based on these data the inventors have proposed a model of PNS development in which SCIP function is required for a normal promyelinating phase, during which the myelin genes are repressed, and the one-to-one relationship of myelinating Schwann cell to axon is established. The end of promyelination is marked by the down regulation of SCIP expression, high levels of myelin gene expression and the morphologic appearance of myelin around axons.

In many respects, regeneration recapitulates peripheral nerve development in that SCIP is re-expressed after peripheral nerve injury, and the myelin genes are transiently down-regulated during Wallerian degeneration. Yet, unlike promyelination, when SCIP is expressed in a tightly restricted manner, SCIP is expressed for extended periods after injury (Scherer et al., 1994). It is difficult to infer the function of this gene product during regeneration from these data, as the expression does not coincide with regenerative changes in the nerve at late stages after crush. The ΔSCIP mice have yielded a great deal of insight into the function of and requirement for SCIP during development.

SUMMARY OF THE INVENTION

The present invention provides a method for regenerating nervous tissue comprising contacting the tissue with an effective amount of Schwann cells expressing ΔSCIP to regenerate the nervous tissue.

The present invention also provides a method for treating a subject in need of nervous tissue regeneration comprising introducing an effective amount of Schwann cells expressing ΔSCIP into the subject to induce nervous tissue regeneration in the subject. The subject in need of nervous tissue regeneration may have a neurodegenerative disease or damaged neurons.

Further provided by the present invention is a method of inducing nervous tissue regeneration in a subject in need of such treatment comprising administering to the subject an effective amount of ΔSCIP to induce nervous tissue regeneration in the subject. The administration of ΔSCIP may be effected by administration of the ΔSCIP protein or the ΔSCIP nucleic acid.

BRIEF DESCRIPTION OF THE FIGURES

FIGS. 1A–1C show that the expression of the ΔSCIP transgene results in accelerated peripheral nerve regeneration. Electronmicrographs one week after crush injury of adult wt (FIG. 1A) or ΔSCIP (FIG. 1B) mice. The samples were prepared from the from the same proximal-distal level in each specimen. There are many profiles of autophagocytosed and destroyed myelin in the wt (asterisks). In contrast, the axons from the ΔSCIP mice show considerable regeneration with thin, new myelin (arrow heads), and a corrugated appearance of the basal lamina (FIG. 1C, arrowheads), both of which suggest extensive regeneration. The corrugated basal laminae are consistent with new axons entering and not yet filling residual endotubes vacated by larger axons after injury. (scale bar=1 μm)

FIG. 2 demonstrates that loss of function correlates with an absence of electrophysiological function in the affected sural nerves after crush. One week following unilateral sciatic nerve crush all operated mice were paralyzed ipsilateral to the nerve crush. Paralysis can result from incomplete transection, therefore in order to determine the completeness of the mechanical transection the inventors assayed for the presence of electrophysiologic activity in sural nerves. There is an absence of electrophysiological response in either the ΔSCIP or wt sural nerve. If there were a delay in degeneration of the nerve distal to the crush injury or partial transection, there would be a measurable response in the sciatic nerve branches. However, no such activity is observed in either strain of mouse.

FIGS. 3A and 3B set forth results of equivalent degeneration in both ΔSCIP and wt mice 10 mm below sciatic nerve crush one week following surgery. Regeneration of peripheral nerves follows a proximal to distal gradient. therefore, the most distal nerve segments are the last to be re-innervated by new axons, and the last to undergo remyelination. The extent of degeneration in wt (FIG. 1A) and ΔSCIP (FIG. 1B) nerves is comparable, at distances in which neither strain had yet effected regeneration. This observation rules out the possibility that there is a delayed degeneration in the animals that express this mutant form of SCIP, as well demonstrating the totality of the nerve crush. A delay in degeneration might account for the profiles observed in FIG. 3A if and only if there was an overall delay in degeneration. Such a delay would be accompanied by sustained electrophysiologic function in the distal branches of the crushed nerve (see FIG. 2) and profiles on intact Schwann cell/axon units, neither of which is the case in these animals.

FIGS. 4A and 4B show axonal and myelin hypertrophy one month after crush. FIG. 4A: The montages are representative sections of sciatic nerve taken at the same axial level from either a wt or a ΔSCIP homozygote, and are displayed at the same magnification (scale bar=1 micron). The axons and associated myelin sheaths of the wt animals have approached the size of the original myelinated axons. However, in the ΔSCIP sciatic nerve the fibers are much larger than those in the wt animals. This is particularly dramatic because the ΔSCIP parent axons are smaller than wt fibers, thereby suggesting that the ΔSCIP Schwann cells are disregulated and are oversupplying trophic support for their associated axons. In addition, the ΔSCIP Schwann cells have grossly over-myelinated their associated axons (asterisks), demonstrating a second disregulation in these cells. FIG. 4B: Axonal growth in the ΔSCIP mice following 1 month of regeneration. A comparison of the axonal cross-sectional areas of myelinated fibers from regenerated nerves demonstrates the large size of the ΔSCIP axons following regeneration (from a 670 $\mu m^2$ area). Several of the ΔSCIP myelinated axons exceed 30 $\mu m^2$, which is much larger than any of the wt myelinated fibers. The comparison of regenerated versus baseline myelinated axonal diameters demonstrates a phenotype switch in the ΔSCIP nerves. These axons transform from abnormally small fibers (ΔSCIP, baseline) to abnormally large axons (ΔSCIP, one month post crush).

FIGS. 5A and 5B demonstrate the over-expression of myelin and axonal proteins in the regenerating ΔSCIP nerve 1 month after crush. FIG. 5A: These are representative Western blots from proteins extracted from equal amounts of protein (15 $\mu$g) from sciatic nerve comparing crushed (lanes 1 and 2) and contralateral, uncrushed (lanes 3 and 4) sciatic nerves from ΔSCIP (lanes 2 and 4) and wt (lanes 1 and 3). These data demonstrate a vast over-expression of $P_0$, neuron-specific tubulin and MBP in the regenerating ΔSCIP nerves 1 month after injury. In comparison, there is roughly an equal amount of Connexin 32 protein in all 4 samples. Sciatic nerve proteins were delipidated, resolved on a 12% SDS gel, and transferred to nitrocellulose membranes. FIG. 5B: A comparison of the density of the Western blotted bands for each of the proteins discussed regarding FIG. 5A, above. The samples are from the injured nerves only.

FIGS. 6A and 6B show the in vitro recapitulation of in vivo accelerated neuronal regeneration is mediated by ΔSCIP Schwann cells. Neonatal rat DRGs were plated on monolayers of either wt (FIG. 6A) or ΔSCIP (FIG. 6B) Schwann cells in saturating levels of NGF (100 ng/ml), and grown for 20 hours. The cultures were fixed and the neurites and neuronal cell soma were stained with a neuron-specific, anti tubulin-antibody, TuJ1. DRG neurons consistently extended more fibers which grew farther on ΔSCIP Schwann cells than on wt Schwann cells.

FIGS. 7A–7C demonstrate that ΔSCIP Schwann cells support process outgrowth by CNS neurons. Neonatal cerebellar granule cell neurons were plated on wt (FIG. 7A) or ΔSCIP Schwann cells (FIGS. 7B and 7C), and allowed to grow for twenty-four hours in serum containing medium (10% fetal calf, 5% horse serum). The cultures were subsequently fixed and stained with a neuron-specific anti tubulin-antibody, TuJ1. The neurons put out extensive networks of fibers, either as single axons (FIG. 7B) or as fasciculated bundles (FIG. 7C).

FIG. 8 shows the results of cerebellar granule cell outgrowth on Schwann cell monolayers.

FIG. 8 shows the results of PC12 cell outgrowth on Schwann cell monolayers.

DETAILED DESCRIPTION OF THE INVENTION

Figure 1A:
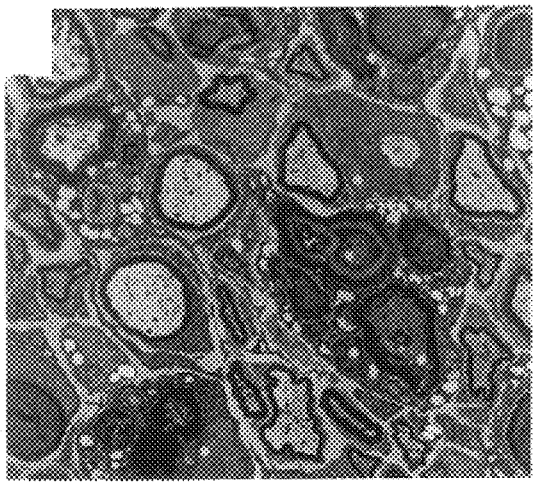
FIGS. 1A–1C.

The present invention provides a method for regenerating nervous tissue comprising contacting said tissue with an effective amount of Schwann cells expressing ΔSCIP to regenerate the nervous tissue.

As defined herein, "nervous tissue" comprises any or all of the following: neuronal cells, Schwann cells, stellate cells, neuroglial cells, granule cells, ganglia cells, grey matter, white matter, myelin, neurolimma, axons, dendrites, motor neurons, fibrils and fibular processes.

As used herein, "neural cells" are any of the cells that constitute nervous tissue and the tissue that supports it including, but not limited to, Schwann cells, stellate cells; neuroglial cells, granule cells and ganglia cells. The granule cells may be cerebellar granule cells or cerebral granule cells.

Inducing "nervous tissue regeneration" is herein defined as inducing one or more of: the myelination of a nerve, the growth of neurons, the growth of the axons or dendrtes of the nerve, the growth of fibrils of neuroglia, the growth of stellate cells, the growth of fibular processes of neuroglia, the remyelination of grey matter, and the remyelination of white matter.

As used herein, "growth" may be defined as an increase in thickness, diameter, and length of the nerve fibers or the myelin or neurolimma coverings, and the supporting fibrils and fibular processes. The definition of "growth" as used herein also includes an increase in the numbers of Schwann cells, stellate cells or neuroglial cells present on or supporting a nerve.

The neuronal regeneration may take place in nerves of both the central nervous system and the peripheral nervous system.

The present invention also provides a method for treating a subject in need of nervous tissue regeneration comprising introducing an effective amount of Schwann cells expressing ΔSCIP into the subject to induce nervous tissue regeneration in the subject. The subject in need of nervous tissue regeneration may have a neurodegenerative disease, damaged neurons and/or damaged myelin.

Non-limiting examples of neurodegenerative diseases which may be treated using the methods described herein are Alzheimer's disease, Pick's disease, Huntington's disease, Parkinsoni's disease, cerebral palsy, amyotrophic lateral sclerosis, muscular dystrophy, multiple sclerosis, myasthenia gravis, and Binswanger's disease.

In addition, damaged neurons or myelin caused by vascular lesions of the brain and spinal cord, trauma to the brain and spinal cord, cerebral hemorrhage, intracranial aneurysms, hypertensive encephalopathy, subarachnoid hemorrhage or developmental disorders may also be treated using the methods provided by the present invention. Examples of developmental disorders include, but are not limited to, a defect of the brain, such as congenital hydrocephalus, or a defect of the spinal cord, such as spina bifida.

Also provided by the present invention is a method of inducing nervous tissue regeneration in a subject in need of such treatment comprising administering to the subject an effective amount of ΔSCIP to induce nervous tissue regeneration in the subject.

The administration of ΔSCIP may be effected by administration of the ΔSCIP protein itself or administration of a nucleic acid encoding ΔSCIP by the use of standard DNA techniques.

The ΔSCIP protein may be administered to a tissue or subject topically or by intravenous, intramuscular, intradermal, subcutaneous or intraperitoneal injection. The ΔSCIP protein is administered in amounts sufficient to promote nervous tissue regeneration in a subject.

The ΔSCIP protein maybe produced synthetically or recombinantly, or may be isolated from native cells, or may be an analogue of the ΔSCIP protein. As used herein, "analogue" means functional variants of the ΔSCIP protein, and includes ΔSCIP protein isolated from mamimalian sources other than human, such as mouse, as well as functional variants thereof.

The nucleic acid sequence encoding ΔSCIP protein administered to a mammal may be genomic DNA or cDNA. The nucleic acid sequence may be administered using a number of procedures known to one skilled in the art, such as electroporation, DEAE Dextran, monocationic liposome fusion, polycationic liposome fusion, proto plast fusion, DNA coated microprojectile bombardment, by creation of an in vivo electrical field, injection with recombinant replication-defective viruses, homologous recombination, and naked DNA transfer. It is to be appreciated by one skilled in the art that any of the above methods of DNA transfer may be combined.

A nucleic acid encoding ΔSCIP protein may also be administered to a mammal using gene therapy, i.e. by the administration of a recombinant vector containing a nucleic acid sequence encoding ΔSCIP protein. The nucleic acid sequence may be, for example, genomic DNA or cDNA. The recombinant vector containing nucleic acid encoding ΔSCIP protein may be administered to a mammal using any number of procedures, known to one skilled in the art, including, but not limited to, electroporation, DEAE Dextran transfection, calcium phosphate transfection, cationic liposome fusion, protoplast fusion, by creation of an in vivo electrical field, DNA coated microprojectile bombardment, injection with recombinant replication-defective viruses, homologous recombinantion; gene therapy, and naked DNA transfer. It is to be appreciated by one skilled in the art that any of the above methods of nucleic acid transfer may be combined. Accordingly, a cell, such as a Schwann cell or a glial cell which expresses ΔSCIP protein introduced therein through viral transduction, homologous recombination, or transfection is also provided by the present invention. This cell may then be administered to a subject to promote nervous tissue regeneration.

The recombinant vector may comprise a nucleic acid of or corresponding to at least a portion of the genome of a virus, where this portion is capable of directing the expression of a nucleic sequence encoding ΔSCIP protein, operably linked to the viral nucleic acid and capable of being expressed as a functional gene product in the subject mammal.

The recombinant vectors may also contain a nucleotide sequence encoding suitable regulatory elements so as to effect expression of the vector construct in a suitable host cell. As used herein, "expression" refers to the ability of the vector to transcribe the inserted DNA sequence into mRNA so that synthesis of the protein encoded by the inserted nucleic acid can occur. Those skilled in the art will appreciate that a variety of enhancers and promoters are suitable for use in the constructs of the invention, and that the constructs will contain the necessary start, termination, and control sequences for proper transcription and processing of the nucleic acid sequence encoding ΔSCIP protein when the recombinant vector construct is introduced into a mammal. Vectors suitable for the expression of the nucleic sequence encoding ΔSCIP protein are well known to one skilled in the art.

It is within the confines of the invention that ΔSCIP protein may be administered in combination with a growth factor to promote nervous tissue regeneration. ΔSCIP, in the form of a protein, nucleic acid, or a recombinant vector containing nucleic acid encoding ΔSCIP, may be administered to a subject prior to, simultaneously with or subsequent to administration of a growth factor.

For the purposes of gene transfer into a tissue or subject, a recombinant vector containing nucleic acid encoding ΔSCIP may be combined with a sterile aqueous solution which is preferably isotonic with the blood of the recipient. Such formulations may be prepared by suspending the recombinant vector in water containing physiologically compatible substances such as sodium chloride, glycine, and the like, and having buffered pH compatible with physiological conditions to produce an aqueous solution, and rendering such solution sterile. In a preferred embodiment of the invention, the recombinant vector is combined with a 20–25% sucrose in saline solution in preparation for introduction into a mammal.

The amounts of nucleic acid encoding ΔSCIP, or nucleic acid encoding ΔSCIP contained in a vector are administered in amounts sufficient to induce nervous tissue regeneration in a subject. However, the exact dosage will depend on such factors as the purpose of administration, the mode of administration, and the efficacy of the composition, as well as the individual pharmacokinetic parameters of the subject. Such therapies may be administered as often as necessary and for the period of time as judged necessary by one of skill in the art.

Non-limiting examples, of tissues into which nucleic acid encoding ΔSCIP may be introduced to induce nervous tissue regeneration include fibrous, vesicular, cardiac, cerebrovascular, muscular, vascular, transplanted, and wounded tissues. Transplanted tissues are for example, heart, kidney, lung, liver and ocular tissues.

The tissues into which nucleic acid encoding ΔSCIP may be introduced to induce nervous tissue regeneration include those associated with neurodegenerative disease or damaged neurons.

Non-limiting examples of neurodegenerative diseases which may be treated using the methods described herein are Alzheimer's disease, Pick's disease, Huntington's disease, Parkinson's disease, cerebral palsy, amyotrophic lateral sclerosis, muscular dystrophy, multiple sclerosis, myasthenia gravis, and Binswanger's disease.

In addition, damaged neurons caused by vascular lesions of the brain and spinal cord, trauma to the brain and spinal cord, cerebral hemorrhage, intracranial aneurysms, hypertensive encephalopathy, subarachanoid hemorrhage or developmental disorders may also be treated using the methods provided by the present invention. Examples of developmental disorders include, but are not limited to, a defect of the brain, such as congenital hydrocephalus, or a defect of the spinal cord, such as spina bifida.

In further embodiments of the invention, ΔSCIP is used to enhance wound healing, organ regeneration and organ transplantation, including the transplantation of artificial organs. In addition ΔSCIP can be used to accelerate and enhance nervous tissue coverage of grafts.

The present invention is described in the following Examples which are set forth to aid in the understanding of the invention, and should not be construed to limit in any way the scope of the invention as defined in the claims which follow thereafter.

Experimental Details Section
A. Materials and Methods:
Surgery

For sciatic nerve crush experiments, the mice were anesthetized and the right flank and leg were shaved and bathed in 70% EtOH. A single incision was made extending from the knee to the dorsal midline. The skin was retracted, the musculature overlying the sciatic nerve was separated and retracted. The sciatic nerve was isolated, and the sciatic notch located. The nerve was crushed 5 mm below the sciatic notch with a #5 Dumont forceps by the application of pressure for 30 seconds. Pressure was released, and then the crush was repeated for an additional 30 seconds. The muscle and the overlying skin were sutured, and the animal was placed into the cage in the left lateral position under warming lights, and allowed to recover for the indicated times [n=12 ΔSCIP (ΔSCIP/+) and 12 wt (+/+CB6f1 animals)].

Electron microscopy

Mice were anesthetized with ip injection of 0.5 cc of 2.5% Avertin/saline before perfusing via the left ventricle. The animals were perfused for 30 seconds at 37° C. with a rat ringers containing heparin (2.0 ml/L, stock is 10,000 units/ml) and 2% lidocaine(3.0 ml/L) followed by 7–10 minutes with 2% glutaraldehyde/1% paraformaldehyde in 0.15M sodium cacodylate, pH 7.2. The primary, fixation was carried out for 2–4 hours total, at 4° C., with 2% glutaraldehyde/1% paraformaldehyde in 0.15M sodium cacodylate buffer, pH 7.2. Tissues were rinsed 6×20' each followed by an overnight rinse at 4° C. in 0.15M sodium cacodylate buffer, pH 7.2. Secondary fixation was carried out for 4 hours at 4° C. in 1% osrnium-tetroxide/1.5% potassium-ferrocyanide in 0.15M sodium cacodylate buffer, pH 7.2. Tissues were rinsed for 3×10' each in Millipore filtered water at 4° C. followed by en bloc staining in 2% uranyl acetate (aq) at 4° C. for 1 hour. At this point the tissues were dehydrated 1×8' each in a graded ethanol series starting with water, 30%, 50%, 70%, 95% followed by 2×10' each in 100% ethanol and finally propylene oxide. After dehydration the nerve tissue was infiltrated with propylene oxide/Durcupan (Fluka Chemika-BioChemika, Ronkonkoma, N.Y.), in a 25/75 ratio for 60' at room temperature. This was followed by 3×120' each in Durcupan resin at room temp. Sciatic nerves were flat embedded in fresh Durcupan resin and polymerized 24–36 hours at 65° C. 1 μm thick sections were stained in Toluidine blue. Silver sections were cut on a Diatome diamond knife and stained with 2% uranyl acetate for 30' at room temp and Reynold's lead citrate for 7'. Thin sections were viewed at 60 kv and photographed on a JEOL 100 CX conventional transmission electron microscope.

Western Blot analysis

Sciatic nerves were removed from both transgenic animals and non-transgenic littermates. The length of the tissue was carefully assessed, and the protein was extracted overnight at 4° C. in 100 mM Tris, pH6.8 and 1% SDS, and then delipidated with ice-cold acetone. The total protein yield was assessed using a BCA kit (Pierce, Rockford, Ill.). Samples were solubilized in standard SDS sample buffer, denatured by boiling, loaded onto a 12% SDS-PAGE gel, and run at a constant 30 mA. The proteins were then transferred to 0.2 μm nitrocellulose paper (Schleicher and Schuell) in a semi-dry blotting apparatus. The blot was stained with amido black (Sigma) to assess protein transfer, and blocked with a solution of 5% nonfat milk, 5% normal goat serum (Gibco, Grand Island, Mich.) in Tris buffered saline, pH 7.5 (TBS), for 1 hour at room temperature. The blots were then exposed for 1 hour at rt to either a polyclonal rabbit anti- $P_0$ (the generous gift of Dr. D. Colman), rabbit anti-MBP (the generous gift of Dr. C. Campagnoni), mab anti Connexin-32 (the generous gift of Dr. E. Hertzberg), or TuJ1 (1:1000, the generous gift of Dr. A. Frankfurter), and after 5 washes exposed to either anti rabbit or anti mouse [$^{125}$I] Ig second antibody, and autoradiographed. $P_0$, TuJ1, MBP and Connexin 32 blots were quantitated on a Molecular, Dynamics STORM Phosphoimager as described (16).

Morphometric analysis

Photographic prints of electronmicrographs, covering identical areas of control and transgenic sciatic nerve, were scanned into an Adobe Photoshop file (Aldus, San Diego, Calif.). Montages were assembled that represented full cross-sectional areas across the nerve, and were then transferred to NIH Image, an image analysis program. The imaged montages were assessed for cross-sectional areas of axons, for axon/myelin complexes and for myelin alone, in 1 mm$^2$ areas. Data manipulation was carried out using the Microsoft Excel program (Microsoft, Redmond, Wash.).

Electrophysiology

The studies were carried out essentially as described by us earlier (Bieri, et al., 1997). In brief, adult mice expressing the ΔSCIP transgene and wild-type litter mate controls were evaluated using peripheral nerve electrophysiologic indices (n=4). In each subject, whole nerve measures of maximal conduction were obtained from the distal sural sensory nerve, both ipsi and contralateral to the crush. Recordings were performed under general anesthesia using ketamine (50 mg/kg, I.P.) and xylazine (40 mg/kg, I.P.) in a sound attenuated and electrically shielded recording chamber. Temperature was maintained using a circulating warm water bath and monitored using rectal and surface probes. Conduction and amplitude measurements were obtained using standard, non-invasive stimulating and recording techniques, as previously described (Maycox et al., 1997).

Cell Culture

Schwann cells were cultured in Dulbecco's modified Eagle's medium (DMEM) with 10% fetal calf serum and 2–4 mM forskolin, as described previously (Lemke et al., 1988). Cultures from individual animals were maintained separately, and each animal was genotyped by PCR which transgene-specific primers spanning the, $P_0$ 5' UTR (5' CGCTCTCTCCACCCCACAGAC 3') (SEQ. ID. NO. 1) to the ΔSCIP transgene (5' GCCGCCTCCCGCCGCCAGCAT 3') (SEQ. ID. NO. 2). Individual cultures grown in DMEM, supplemented with 10% FCS and antibiotics and were expanded in the presence of 1 μM forskolin and 50 μg/ml of GGF. For the DRG axonal outgrowth assays, the Schwann cells were split into 60 mm dishes and cultured in DMEM supplemented with 1% FCS and 0.5% horse serum without forskolin or GGF for 3 days prior to the addition of the DRGs. One day prior to the addition of the rat DRGs to the cultures, the cells were switched to DMEM supplemented with 1% FCS and 0.5% horse serum and 100 ng/ml of recombinant NGF. Brachial and lumbar DRGs were harvested from post-natal day 0 Sprague Dawly rats, stripped and added to the cultures in fresh medium -with added NGF (100 ng/ml). Cultures were allowed to grow an additional 20 hours and were then fixed in 4% paraformaldehyde. The cells were permiablized and blocked in 10% NGS/0.1% Triton X100 for 1 hour. TuJ1, a monoclonal antibody that recognizes the neuron-specific beta III tubulin isoform (the generous gift of A. Frankfurter) was added at 1:1000 at 4° C. overnight, washed x5 in PBS/0.01% Triton X100, and exposed to goat anti-mouse/biotin for 1 hour at room temperature (Vector Labs). The cells were washed x5 in PBS/0.01% Triton X100 and the antibody was visualized using the ABC elite system with DAB and Nickel from Vector Laboratories.

B. Results

ΔSCIP Peripheral Nerves Regenerate More Rapidly

Figure 1B:
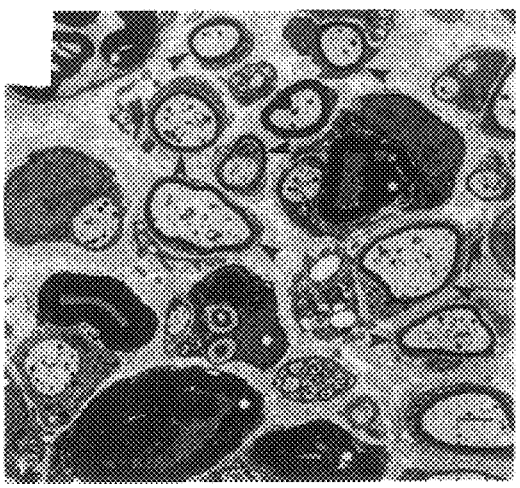
Figure 1C:
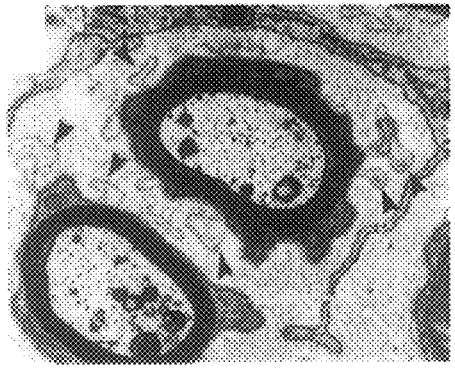

The sciatic nerves of either adult wild-type (wt) or ΔSCIP mice were crushed, and the animals allowed to recover for 1 week. This time was selected because of the extensive degeneration distal to the crush point in wt animals, as has been reported (Aguayo et al., 1973). The injured nerves were examined at 5 mm below the crush site. In our hands this distance from the crush site is largely free of new axons or new myelin one week after injury. This is not unexpected even though established axons can grow at rate of up to 1 mm/day (Hoffman and Lasek, 1975): the rate of growth cone extension is dependent upon numerous factors including intracellular calcium (Kater et al., 1988), growth factor concentration (Gundersen and Barrett, 1980) and extracellular matrix composition (Walter et al., 1990). In combination these factors, limit the overall rate of axonagenesis during regeneration as axon elongation is dependent upon growth cone extension. Electronmicrographs of wt nerve (FIG. 1A) demonstrated many dead and dying axons, numerous profiles of Schwarin cells autophagocytosing myelin (1A, asterisks), and an absence of regenerative profiles. The myelinated axons which were present had an appearance of being in the early stages of degeneration, as shown by their crenated morphology. In contrast, examination of the ΔSCIP mice at the same distance relative to the crush revealed an extensive degree of regeneration (FIG. 1B), characterized by the appearance of thin, new myelin (1B, arrowheads), and corrugated basal lamina (bands of Buingnrer) (FIG. 1C), (herein termed "endotubes"). The corrugated, flaccid morphology of endotubes is due to the failure of the newly regenerated axons to attain a sufficient size to fill out the original volume of the endotubes. Over time, these axons and their associated myelinating Schwann cells will completely fill the endotubes, with an associated loss of the corrugated appearance of the basal lamina. The regenerating profiles, with the characteristic basal larnina seen in the ΔSCIP nerves present a markedly different appearance in contrast with the remaining myelinated axons in the wt mice, in which the basal lamina is still closely apposed to the myelin sheath. The unruffled appearance of the basal lamina in the wt mice is consistent with these being the original, myelinated fibers. Importantly, the axons from the ΔSCIP animals appear to be quite healthy, even at this early time point, with an apparent normal complement of cytoskeletal filaments and mitochondria (FIG. 1C). Numerous profiles of regenerating structures were observed and Schwann cells autophagocytosing their myelin (FIG. 1B, asterisks). Profiles of both degenerating and regenerating fibers were present in the ΔSCIP animals, while only degenerating fibers were noted in the wt nerve. Table 1 demonstrates the difference in distributions of regenerating and degenerating axons in both the wt and ΔSCIP animals after crush injury. In order for a fiber to be considered a regenerating myelinated axon, the profile had to be ensheathed and wrapped by a thin myelin organelle, and be surrounded by a corrugated basal lamina. Such a structure is consistent with being an endotube remaining from larger myelinated axon. It is noteworthy that the regenerating fibers are randomly dispersed amid profiles of degenerating axons, suggesting that the entire field has suffered extensive injury. As can be seen in the table, there is an absolute absence of regenerating myelinated fibers in the nerves of wt animals 1 week and 5 mm below the crush.

Figure 2:
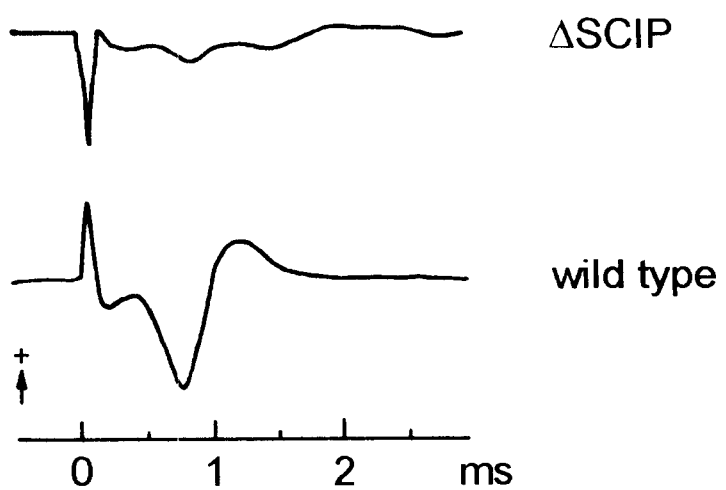
FIG. 2.
Figure 3A:
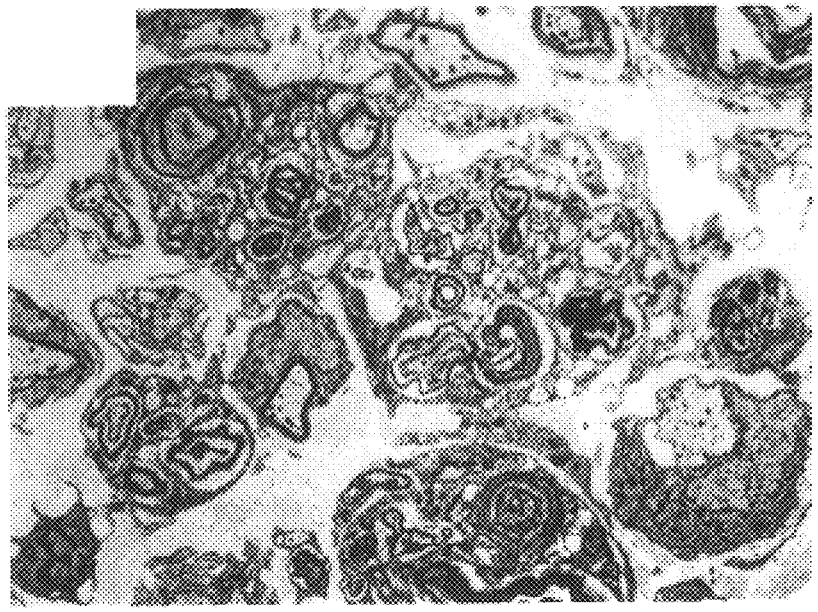
FIGS. 3A and 3B.
Figure 3B:
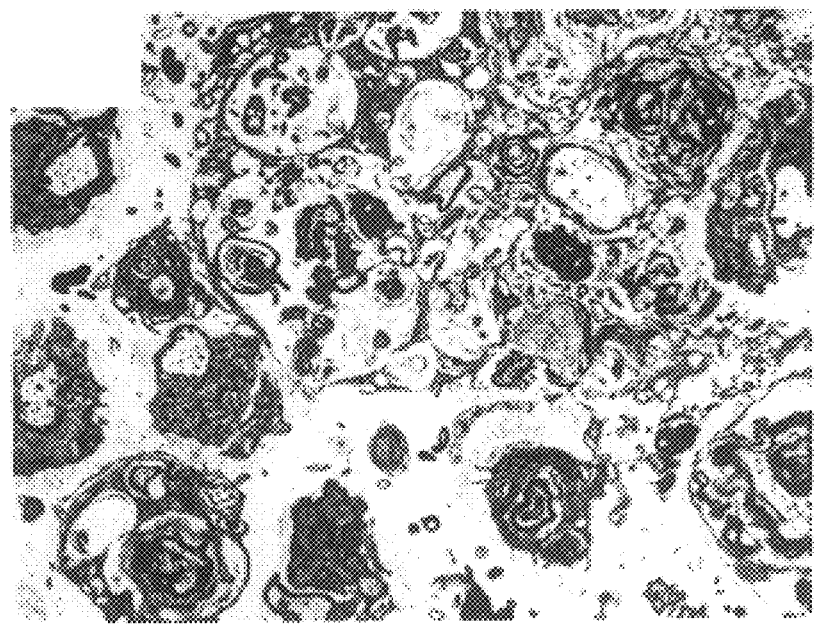

Both transgenic and wt animals were paralyzed ipsilateral to the crush. Partial paralysis can result from incomplete transection, but can appear to be a complete paralysis based on observation. In order to demonstrate that the paralysis observed in the operated mice was the result of complete mechanical axotomy and an associated loss of nerve function below the injury site, the inventors have conducted electrophysiological testing of the animals 1 week after injury (n=4). These studies revealed an absence of nerve conduction in the sural nerves of the animals, further suggesting the completeness of the mechanical transection, and showing that regeneration had not yet advanced to the lower limb (FIG. 2). If the ΔSCIP mice had failed to degenerate in a timely manner, one might expect a retained physiologic activity in the distal nerve in spite of the transection, which we failed to document. Contralateral to the injury, the animals had baseline conduction studies, consistent with exaggerated responses the inventors have recently reported for the ΔSCIP mice (Bieri et al., 1997) (data not shown). Finally, the inventors have compared very distal regions to verify that the inventors are in fact documenting accelerated regeneration in the proximal nerve, as opposed to delayed degeneration, as is seen in the ola mouse (Crawford et al., 1995; Glass et al., 1993; Glass and Griffin, 1994). At sites ~10 mm below the injury, wt and ΔSCIP nerves are, indistinguishable with respect to the degree of degeneration and the absence of regenerating profiles (FIG. 3). Taken en masse, the data show the crush injuries were complete, Wallerian degeneration had occurred as expected with an associated paralysis, and there was an established active axonal and myelin regeneration only in the ΔSCIP nerves at this early time point after crush. This is the first in vivo demonstration of a genetically controlled acceleration of peripheral nerve regeneration.

The ΔSCIP transgene is expressed uniquely in the Schwann cells (Weinstein et al., 1995), and its effect on the accelerated axonal regeneration must therefore be indirect. This is consistent with previous observations that Schwann cells are both required for and are mediators of regeneration. Based on the above data it is clear that Schwann cells are capable of regulating the rate, as well as the extent of regeneration. These data were true of two lines of ΔSCIP transgenic animals, ΔSCIP Line 1 and Line 2. The data reported here are entirely from Line 1, but have been, demonstrated experimentally in both lines of ΔSCIP mice, thus ruling out the possibility that the described phenomenon is the result of a insertional event.

TABLE 1

Regenerating Myelinated Axons 1 Week After Mechanical Transection

| Regenerating profiles (R) | Degenerating profiles (D) | R/D |
|---|---|---|
| wild-type 0 | 458 | 0 |
| ΔSCIP 357 | 284 | 1.257 |

Table 1. Accelerated regeneration in the ΔSCIP animals 1 week after crush. We have examined numerous fields of either wt or transgenic nerves 5 mm below the site of a mechanical transection. Table 1 presents an enumeration of total regenerating and degenerating profiles, and calculate the ratio of new to dying fibers. In order to be considered a regenerating fiber the axon had to be ensheathed and wrapped by a thin myelin organelle, and be surrounded by a corrugated basal lamina. In contrast, the profiles were deemed to be dead or dying by the presence of decaying or phagocytosed myelin, condensed axoplasmic contents and/or a crenated appearance.

Axonal and Myelin Hypertrophy Mediated by the ΔSCIP Transgene

Figure 4A:
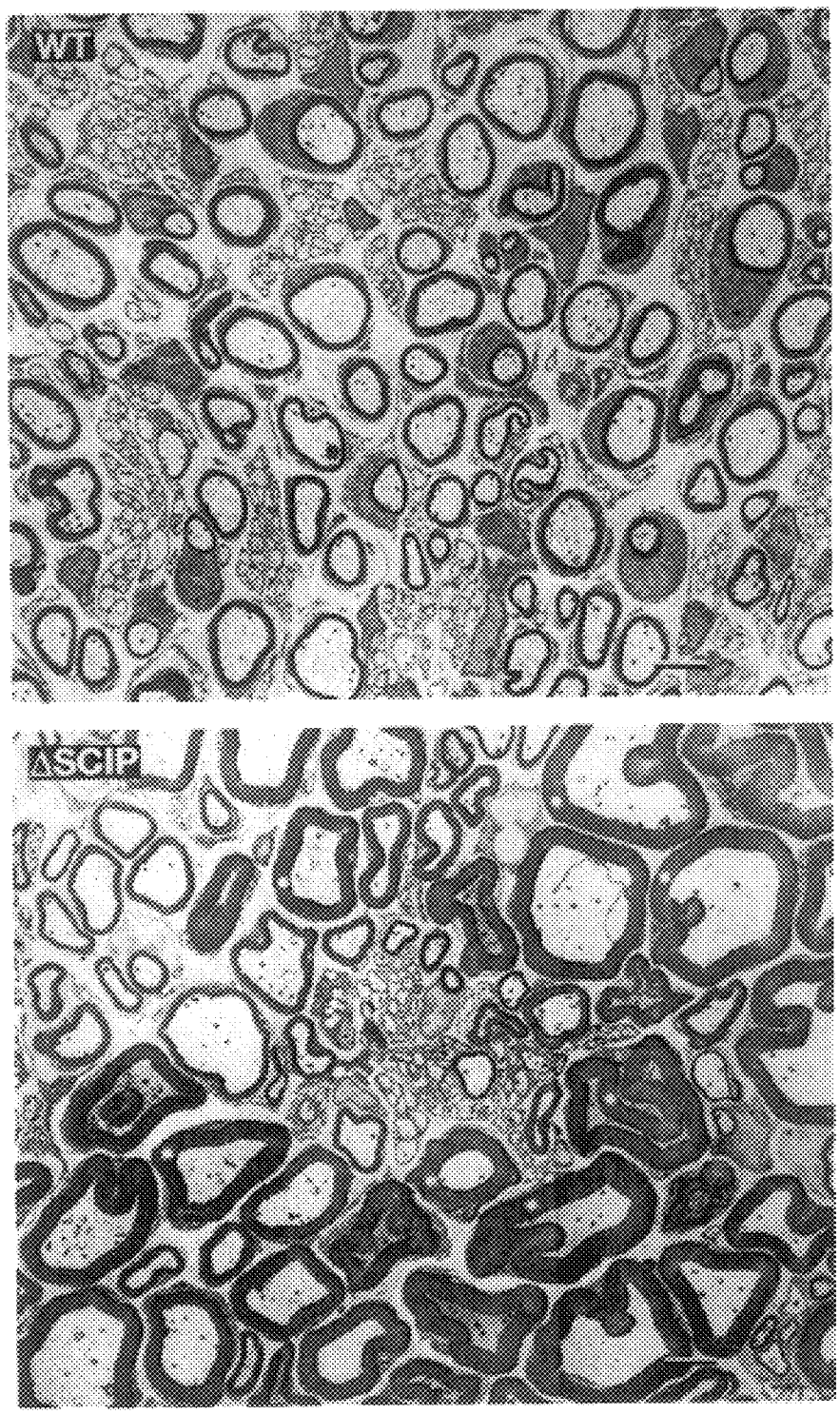
FIGS. 4A and 4B.
Figure 4B:
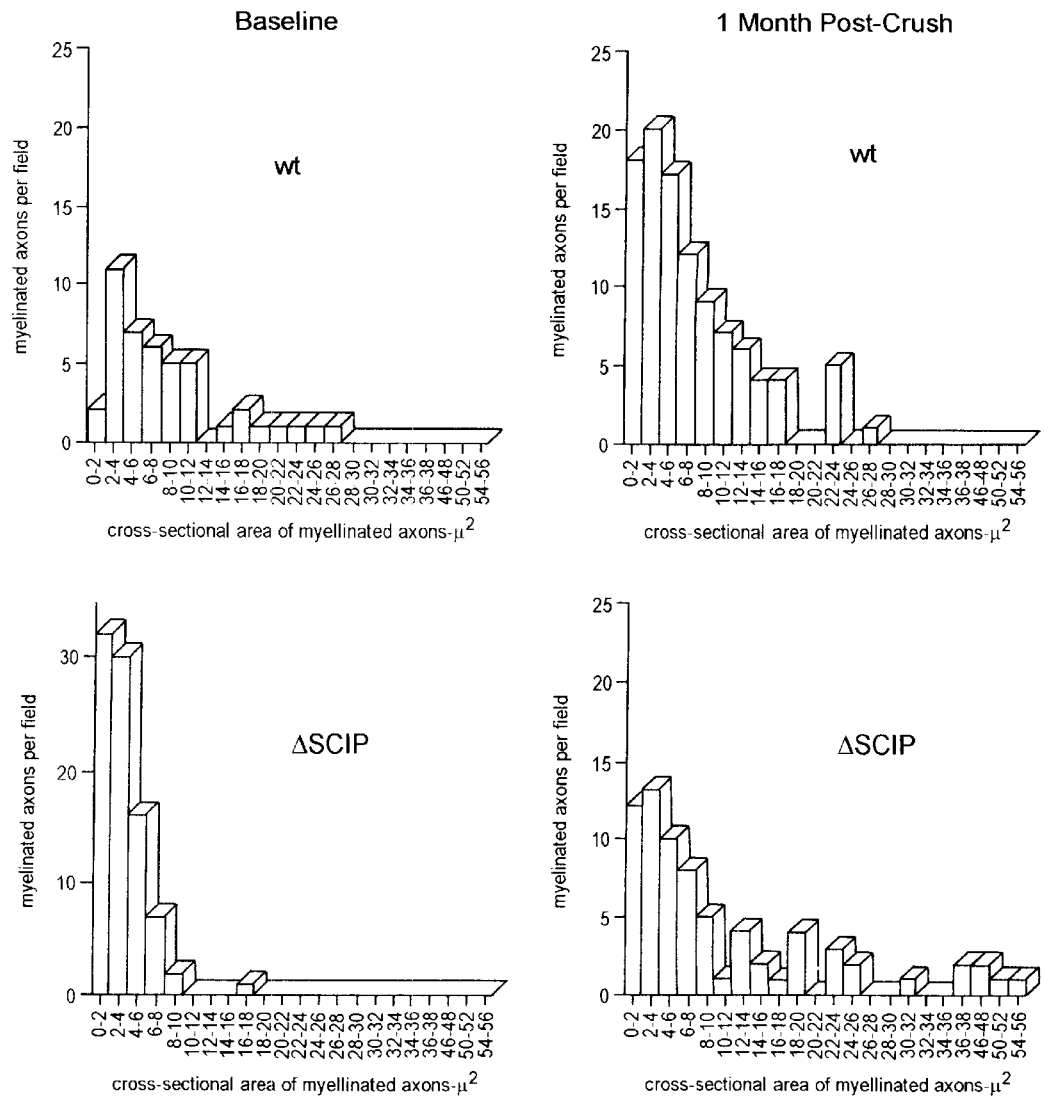
Figure 5A:
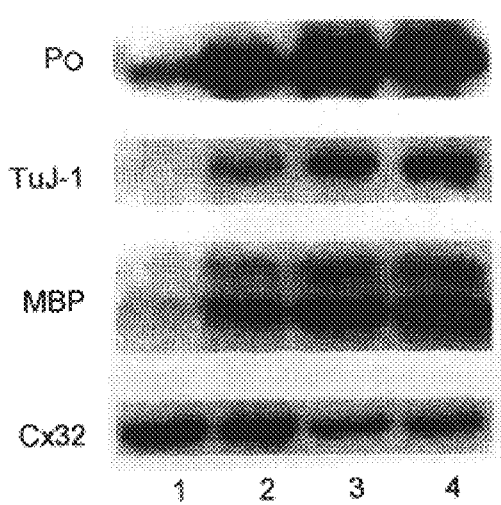
FIGS. 5A and 5B.
Figure 5B:
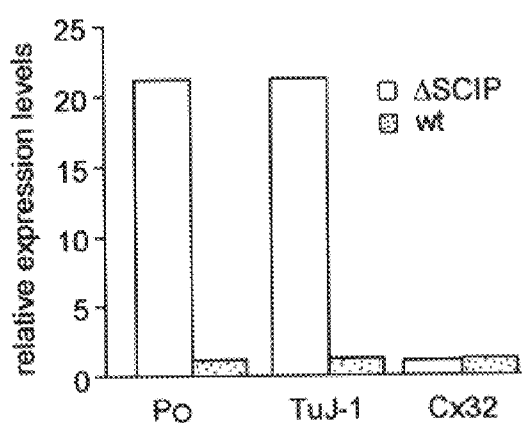

The long term consequences of the expression of the ΔSCIP transgene on the regenerating peripheral nerve were considered. To test this, sciatic nerve crush surgery was performed on wt and ΔSCIP animals, waited 30 days, and harvested tissue for both biochemical assessment and electron microscopy. As expected, one month after injury the wt nerve has largely regenerated (FIG. 4-wt). The axons have approached the size of the parent fibers (see FIG. 4B), and they were extensively myelinated. The thickness of this myelin is consistent with the previously described linear relationship between axonal diameter and myelin thickness (Friede and Samorajski, 1967). In contrast, the axons from the ΔSCIP animals have grossly surpassed their baseline dimensions (FIG. 4-ΔSCIP and 4B). The axons in these animals have hypertrophied such that their axonal diameters have not only overtaken the parent fibers, but have also grown well beyond the size of the wt axons (Weinstein et al., 1995) (compare histograms in FIG. 4B). These data represent a radical change in the phenotype of the axons of the mutant animals in that they have progressed from significantly smaller than wt prior to injury, to much larger than wt axons after regeneration. Given the exaggerated size of the ΔSCIP axons following injury, it is not surprising that the inventors found 21 times the level of neuron-specific tubulin in the ΔSCIP nerve preparations (FIGS. 5A & B). By definition this axonal hypertrophy must be an indirect effect of the ΔSCIP Schwann cells they, and they alone express the transgene (Weinstein et al., 1995), and it suggests an upregulation of Schwann cell-derived trophic support.

The myelin surrounding these fibers has also grossly hypertrophied, such that there was far more myelin per unit size axon than is expected (compare the two panels in FIG. 4A)(Friede and Samorajski, 1967). This is consistent with, but an exaggeration of the phenotype of the naive ΔSCIP animals in which the myelin is mildly hypertrophied with 150–200% more $P_0$ protein than in wt animals (Weinstein et al., 1995). Quantitative Western blotting of nerve-derived proteins 1 month after injury revealed that the ΔSCIP sciatic nerves express 2100% of the level of $P_0$ protein as compared to wt nerves at the same point in regeneration (FIGS. 5A & B). In addition, myelin basic protein (MBP) expression is also dramatically elevated in the regenerating ΔSCIP mice. Interestingly, not all ΔSCIP Schwann cell proteins have elevated expression patterns following regeneration. Connexin 32 is present at roughly the same level in both injured and contralateral nerves, and is the same in both wt and ΔSCIP animals (FIGS. 5A & B). This finding suggests that there are specific myelin-associated genes that are regulated by the SCIP pathway, while other myelin-associated genes lie outside of activation this pathway. The changes in morphology and up-regulation of specific proteins do not appear to be the resulting dramatic changes in expression of the ΔSCIP transgene itself, which was at equivalent levels ipsi-and contralateral to the lesion (data not shown).

Figure 6A:
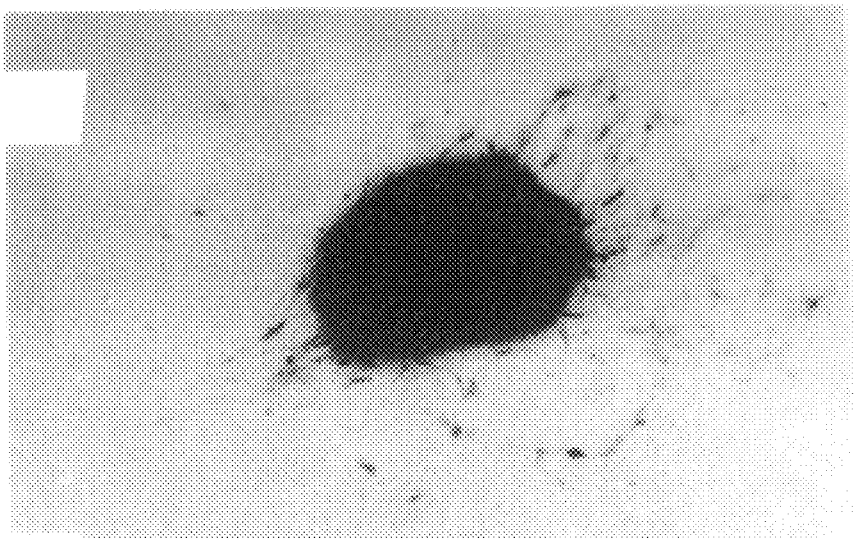
FIGS. 6A and 6B.
Figure 6B:
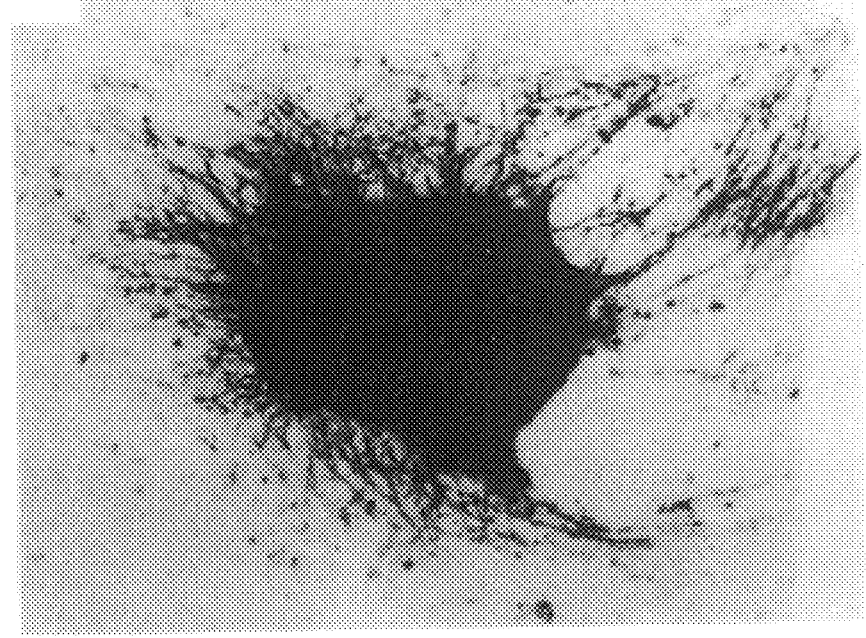
Figure 7A:
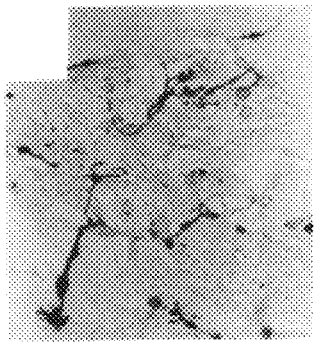
FIGS. 7A–7C.
Figure 7B:
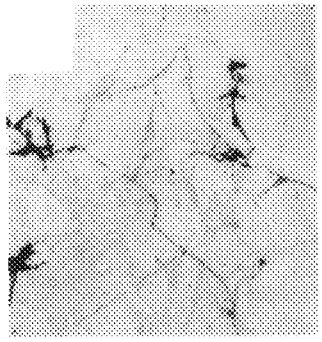
Figure 7C:
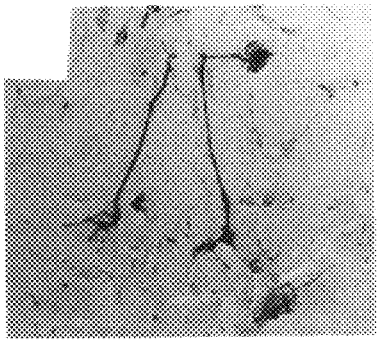
Figure 8:
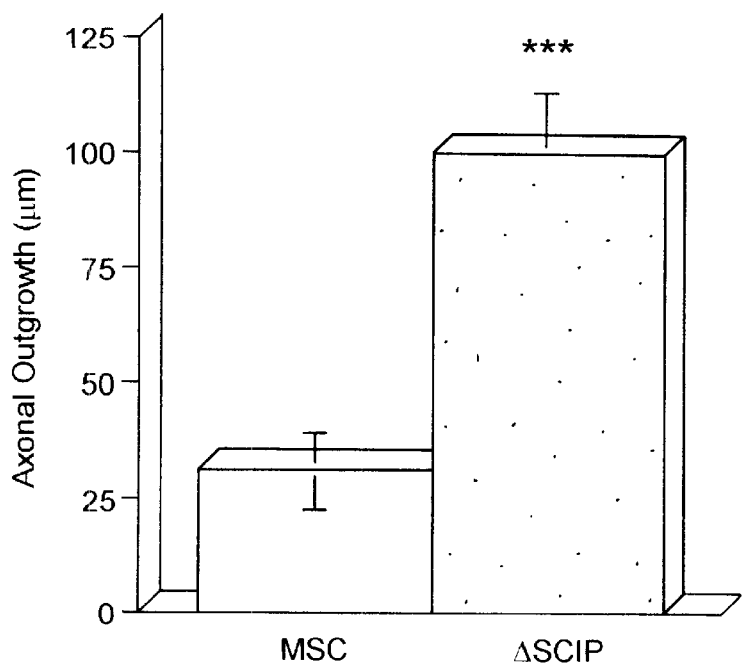
FIG. 8.
Figure 9:
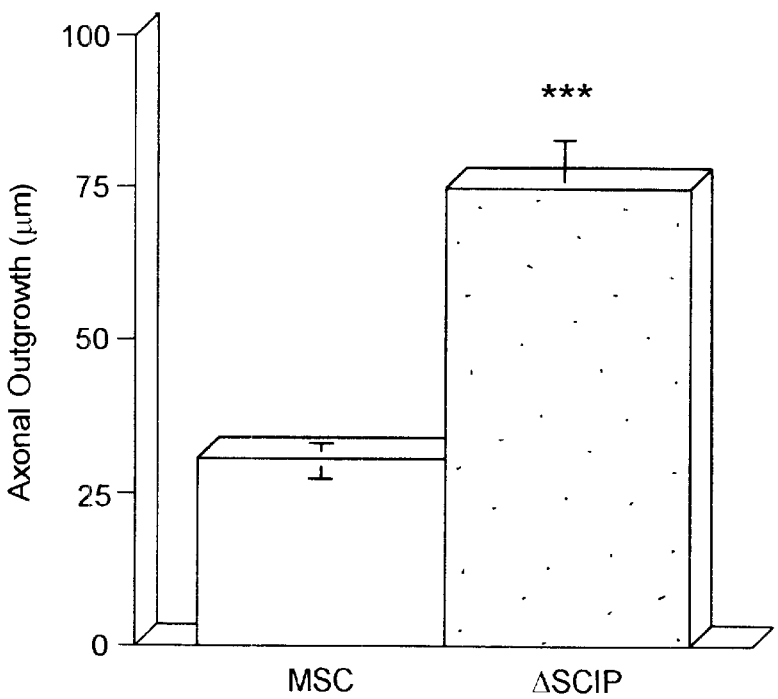
FIG. 9.

ΔSCIP Schwann Cells Promote Axonal Outgrowth In Vitro In order to directly test the possibility that the ΔSCIP Schwann cells are the source of axon regeneration-promoting activity, the inventors established cultures of either ΔSCIP Schwann cells or Schwann cells from wt littermates on postnatal day 2 as described (Brockes and Raff, 1979). Explants of neonatal ($P_0$) rat dorsal root ganglia (DRG) were harvested and cultured on top of the Schwann cell monolayers in the presence of saturating levels of nerve growth factor (NGF) (100 ng/ml) in low serum containing medium (1% FCS/0.5% horse serum). Twenty hours after co-culturing, the cells were fixed and stained with TuJ1, an antibody that recognizes neuron-specific tubulin (Easter et al., 1993) and therefore stains the DRG axons. Rat DRG neurons cultured on ΔSCIP Schwann cells have a greater number of axons, and these axons grow much farther than those from DRGs cultured on wt Schwann cells (compare FIGS. 6A with 6B). The inventors have tested the ΔSCIP Schwann cells for over-expression of a number of molecules known to promote axonal survival and outgrowth. These include brain derived neurotrophic factor (BDNF), neurotrophin 3 (NT-3), cilliary neurotrophic factor (CNTF), nerve growth factor (NGF), glial growth factor 2 (GGF2) and laminin, none of which is expressed above wt levels by the ΔSCIP cells (data not shown). Based on these data, the inventors believe that the ΔSCIP Schwann cells may be a convenient source of molecule(s) that have axon promoting properties distinct from those currently described in the literature. The outgrowth promoting activity is recoverable in the supernatant taken from cultured ΔSCIP Schwann cells. This activity is heat and trypsin sensitive, and is retained on 50 Kd cut-off filters, all of which suggest that activity is dependent upon intact proteins.

C. Discussion

In these studies described herein, the inventors have sought to understand the function of SCIP during peripheral nerve regeneration in a crush lesion model. SCIP is normally re-expressed by the Schwann cells after the regenerated axons contact them (Zorick, 1996). However, unlike the developing nerve, when SCIP is down regulated by the myelinating Schwann cells, its expression is maintained in the regenerated myelinating Schwann cells (Scherer et al., 1994). The experiments were carried out in the ΔSCIP transgenic animals which express the POU domain of SCIP. The perturbation of SCIP function by the expression of the ΔSCIP in these animals results in a dramatic increase in both the rate and extent of peripheral nerve regeneration. One week after experimental nerve crush the axons from ΔSCIP transgenic animals have re-entered at least 5 mm into the distal nerve and they have been re-myelinated. In contrast at the same timepoint and distance from the lesion, the wt animals were still actively undergoing degeneration without evidence of regeneration. When the experiments were carried out for one month following nerve injury, the ΔSCIP animals had vastly hypermyelinated the regenerated nerve, making >20 times the amount of $P_O$ protein as made by wt animals at the same stage of healing, which far exceeds the amount of myelin protein that the wt animals will ever make. The super-induction of the myelin structural genes in the regenerated ΔSCIP nerves is consistent in kind but not extent with our previous results. Those data demonstrated the myelin repressor function of SCIP was antagonized by the ΔSCIP transgene, which resulted in a 2-fold peripheral nerve hypermyelination by the ΔSCIP animals during development. However, the regenerated ΔSCIP nerve had 21 times the amount of $P_O$ protein when compared against the regenerated wt nerve. The exaggerated expression of the myelin proteins is consistent with the over-elaboration of the regenerated myelin organelle in the ΔSCIP animals. The observation that not all myelin genes are upregulated in this model demonstrates the specificity of the system, and suggests numerous regulatory controls in the complex interactions of Schwann cells and axons.

Taken together, the continuous expression of wt SCIP following nerve injury (Scherer et al., 1994) and the data presented in this report suggest that SCIP function is required for the establishment and maintenance of the regenerated myelin sheath it also suggests that the Schwann cell in the regenerated nerve is intrinsically different from the original myelinating Schwann cell, in which SCIP is only transiently expressed and transiently required. Further, these data suggest that the requirements for myelin homeostasis change between baseline, when SCIP is absent, and regeneration, when SCIP is expressed, and it implies that SCIP is limiting in the regenerated peripheral nerve. The inventors have also documented indirect effects on the myelinated axons. The observed axonal hypertrophy represents a phenotypic switch between baseline (small axons) and regeneration (large axons). The very large axons appear to be healthy with a full array of filaments and mitochondria. These findings suggest a heightened level of Schwann cell-derived trophic support of the regenerated axons in the ΔSCIP mice, which is supported by data from in vitro neurite outgrowth studies, where the ΔSCIP Schwann cells were far superior to wt Schwann cells in promoting axonagenesis.

The inventors have previously demonstrated that SCIP represses the $P_O$ and MBP genes, and that this repression is critical for the development of a normal peripheral nerve histoarchitecture and function (Bieri et al., 1997; Weinstein et al., 1995). However in light of the data presented herein, it is difficult to posit a model in which the failure to repress myelin structural genes alone would result in the acceleration of regeneration, axonal hypertrophy and the super-induction of myelin genes we observed. Alternatively, the inventors believe that SCIP may be acting as a bifunctional molecule, depending on the state of the Schwann cell: a transcriptional repressor during development and a transactivator during regeneration. There is precedent for a positive transcriptional role for SCIP in the transactivation of the α3 subunit of the acetylcholine receptor in neuronal cells via its POU domain. (Fyodorov and Deneris, 1996). Notably, this is the domain of SCIP which is preserved in the ΔSCIP mutation. Diametrically opposed functions for SCIP in the same cell type have previously been postulated by Faus and colleagues in the keratinocyte, in which the activity of SCIP was inferred to differ depending on the state of the keratinocyte (Faus et al., 1994). The inventors favor a hypothesis that in the regenerating Schwann cell, the ΔSCIP transgene, in consort with native SCIP, is behaving as a positive regulator of axon promoting molecules, and possibly the myelin structural genes themselves. Whether the bifunctionality of SCIP results from a change in the expression pattern of interacting factors, a change in chromatin structure or both is actively under investigation.

If the ΔSCIP Schwann cells offer superior support for the axon, as demonstrated here, it raises the question of why the axons in the naive ΔSCIP peripheral nerve are smaller than wt fibers. Based on the observation that there is extensive en utero myelination in the ΔSCIP pups, when both the fibers and the animals are still quite small (Weinstein et al., 1995), the inventors reason that the developing axons are physically constrained and are unable to overcome the barrier that many turns of myelin pose. These immature, small axons would therefore be prevented from attaining there full potential diameter. Relief of that constriction, as demonstrated here by removal of the myelin sheath via a crush lesion, enables the axons to grow to their full size potential, which appears to be larger than wt fibers. Presumably the enlargement of the axons in the transgenic animals is under the control of Schwann cell-derived trophic support. Identification of the nature of this outgrowth promoting activity will allow us to test these hypotheses more directly.

The data presented here are suggestive of possible therapeutic modalities in human disease. Schwann cells from sural nerve biopsies can be harvested, purified and expanded in culture (Morrissey et al., 1995) and thus are susceptible to genetic manipulation in vitro. The human homologue of SCIP has been cloned and it is >90% identical to both rat and mouse SCIP (Tobler et al., 1993). The introduction of a human variant of the ΔSCIP transgene can be accomplished by either transfection or retroviral infection, and the altered Schwann cells can be used in an autologous transplantation paradigm. This type of approach might be useful in peripheral nerve regeneration as well as spinal cord trauma. Schwann cells invade the spinal cord and myelinate central axons (Blight and Young, 1989) as well as permit restored function (Gilmore and Duncan, 1968; Snyder et al., 1975) after spinal cord injury, making this an attractive model system to test the axon promoting activity of the ΔSCIP Schwann cells.

ΔSCIP Peripheral Nerves Regenerate More Rapidly

The inventors previously demonstrated that SCIP function is required throughout promyelination. Antagonism of the wt type SCIP protein mid-promyelination results in attenuation and a precocious transition to a myelinating phenotype. In response to PNS injury, SCIP is re-expressed. However, unlike development when SCIP expression is limited to a narrow temporal window, its expression after PNS injury is stable. This raises interesting questions with regard to the SCIP-mediated repression of the myelin genes, and whether SCIP has the same or different functions after injury, when inyelinating is complete, regardless of the presence of SCIP protein. In order to study the role of SCIP during regeneration, the inventors crushed the sciatic nerves of both ΔSCIP and wild-type (wt) mice, and observed their recovery over time.

The initial observations of the inventors were made one week after a crushing transection of the nerve. This time was selected because of the extensive degeneration distal to the crush point in wt animals, as has been reported (Aguayo, et al., *Journal of Neuropathology & Experimental Neurology*, 32:256–70). The inventors examined injured nerves at 5 mm below the crush site. This distance from the crush site is largely free of new axons or new myelin one week after injury. This is not unexpected, even though established axons can grow at rate of up to 1 mm/day (Hoffman, et al., *Journal of Cell Biology*, 66:351–66): the rate of growth cone extension is dependent upon numerous factors including intracellular calcium (Kater, et al., *Trends in Neurosciences*, 11:315–21), growth factor concentration (Gundersen, et al., *Journal of Cell Biology*, 87:546–54) and extracellular matrix composition (Walter, et al., *Trends in Neurosciences*, 13:447–52). In combination, these factors limit the overall rate of axonogenesis during regeneration as axon elongation is dependent upon growth cone extension. Electronmicrographs of wt nerve demonstrated many dead and dying axons, numerous profiles of Schwann cells autophagocytosing myelin, and an absence of regenerative profiles. The myelinated axons which were present had an appearance of being in the early states of degeneration, as shown by the crenated morphology. However, examination of the ΔSCIP mice at the same site relative to the crush, revealed an extensive degree of regeneration, characterized by the appearance of thin, new myelin, and corrugated basal lamina, (herein termed "endotubes"). The corrugated, flaccid morphology of endotubes is due to the failure of regenerated axons to grow sufficiently to fill out the original volume of the endotubes. Over time, the axons and the myelinating Schwann cells will completely fill the endotubes (see below). Thus must be contrasted with the remaining myelinated axons in the wt mice in which the basal lamina is still closely apposed to the myelin sheath. In order for a fiber to be considered a regenerating myelinated axon, the profile had to be ensheathed and wrapped by a thin myelin organelle, and be surrounded by a corrugated basal lamina. Such a structure is consistent with being an endotube remaining from a larger myelinated axon. The unruffled appearance of the basal lamina and the crenated morphology observed in the wt mice is consistent with these being the original, myelinated fibers which are still undergoing degenerative changes. Importantly, the axons from the ΔSCIP animals appear to be quite healthy, even at this early time point, with an apparent normal complement of cytoskeletal filaments and mitochondria. It is noteworthy that the regenerating fibers are randomly dispersed amid profiles of degenerating axons, suggesting that the entire field has suffered extensive injury. In addition, both transgenic and wt animals were paralyzedipsilateral to the crush. In order to demonstrate that the paralysis was consistent with complete axotomy, the inventors have conducted electrophysiological testing of the animals 1 week after injury (n=4) (data not shown). These studies revealed an absence of nerve conduction in the sural nerves of the animals further demonstrating the completeness of the mechanical transection, and suggesting that regeneration had not yet advanced to the lower limb. The inventors have anecdotal evidence that by two weeks there was a reestablishment of sensory function, as assessed electrophysiologically (for an in-depth analysis of the electrophysiology of the ΔSCIP animals see (Bieri, et al., *J. Neuroscience Res.*, 50:821–828)). Taken together these data suggest that the crush injury was complete and that Wallerian degeneration had occurred as expected. The extent of neural recovery post-crush demonstrated by the ΔSCIP mice, when compared to the wt mice, leads us to conclude that the ΔSCIP mice have an accelerated rate of peripheral nerve regeneration. This is the first in vivo demonstration of a genetically controlled acceleration of peripheral, nerve regeneration. The ΔSCIP transgene is expressed uniquely in the Schwann cells (Weinstein, et. al., *Molecular &Cellular Neurosciences*, 6:212–29), and its effect on the accelerated regeneration evidenced here, must be indirect. This is consistent with previous observations that Schwann cells are both required for an are mediators of regeneration. However, our findings indicate that the Schwann cell is capable of regulating the rate, as well as the extent of regeneration (see below). These date were true of two lines of ΔSCIP transgenic animals, ΔSCIP Line 1 and Line 2. The data reported here are entirely from Line 1, but have been demonstrated experimentally in both lines of ΔSCIP mice.

Axonal and Myelin Hypertrophy Mediated By the ΔSCIP mice

The inventors next considered the long term consequences of the expression of the ΔSCIP transgene on the regenerating peripheral nerve. Wild type and ΔSCIP sciatic nerves were crushed, and after 30 days, tissue was harvested for electron microscopy. One month after injury the wt nerve was largely regenerated. The wt axons had approached the size of the parent fibers, and they were extensively myelinated. The thickness of this myelin is consistent with the previously described linear relationship between axonal diameter and myelin thickness (Friede, et al., *Journal of Comparative Neurology*, 134:223–31). In contrast, the axons from the ΔSCIP animals had grossly surpassed their baseline dimensions. The axons in these animals had hypertrophied such that their axonal diameters have not only overtaken the parent fibers, but have also grown well beyond the size of the wt axons (Weinstein; et al., *Molecular & Cellular Neurosciences*, 6:212–29). This represents a radical change in the phenotype of the nerves of the mutant animals in that the axons in the ΔSCIP peripheral, nerves have progressed from smaller than wt prior to injury to larger than wt after regeneration. The axonal hypertrophy must be an indirect effect of the ΔSCIP Schwann cell because only these cells express the transgene, suggesting an upregulation of Schwann cell-derived trophic support.

ΔSCIP Schwann Cells Promote Central and Peripheral Axonal Outgrowth in vitro

In order to directly test the possibility that the ΔSCIP Schwann cells are the source of axon regeneration-promoting activity, the inventors established cultures of either ΔSCIP Schwann cells or Schwann cells from wt littermates on postnatal day 2 as described (Brockes, et al., *In Vitro*, 15:772–8). Explants of neonatal ($P_0$) rat dorsal root ganglia (DRG) were harvested and cultured on top of the Schwann cell monolayers in the presence of saturating levels of nerve growth factor (NGF) (100 ng/ml) in low serum containing medium (1% FCS/0.5% horse serum). Twenty hours after co-culturing, the cells were fixed and stained with TuJ1, an antibody that recognizes neuron-specific tubulin (Easter, et al., *Journal of Neuroscience*, 13:285–99) and therefore stains, the DRG axons. Rat DRG neutrons cultured on ΔSCIP Schwann cells have a greater number of axons, and these axons grow much farther than those from DRGs cultured on wt Schwann cells. In order to generalize the outgrowth and promoting activity of the ΔSCIP Schwann cells the inventors have recently tested their support of central neurons in process formation. Cerebellar granule cell neurons were isolated to virtual purity from postnatal 2 rats, as previously described (Weinstein, et al., *Glia*, 3:130–9, Weinstein et al., *Journal of Cell Biology*, 112:1205–13). Twenty-four hours after plating these cells onto monolayers of wt or ΔSCIP Schwann cells, the cultures were fixed and stained for class III beta tubutin, as above. There is little to no axonal outgrowth on wt Schwann cells, whereas there is both fine, single process extension and fascicles central axons on the ΔSCIP Schwann cells. These data demonstrate that the ΔSCIP transgene mediates a Schwann cell that promotes both peripheral and central neuronal axonogenesis. This is a critical activity for harnessing the ΔSCIP effect as a potential therapeutic in lesions of the spinal cord or brain.

The inventors tested the ΔSCIP Schwann cells for overexpression of a number of molecules known to promote, axonal survival and outgrowth. These include BDNF, NT-3, CNTF, NGF, GGF2 and laminin, none of which is expressed above wt levels by the ΔSCIP cells (data not shown). Based on these data, the inventors believe that the ΔSCIP Schwann cells may be a convenient source of molecule(s) that have axon promoting properties distinct from those currently described in the literature. The outgrowth promoting activity is recoverable in the supernatant taken from cultured ΔSCIP Schwann cells. This activity is heat and trypsin sensitive, and is retained on 50 kD cut-off filters, all of which suggest that activity is dependent upon intact proteins. The inventors have succeeded in a partial purification of this activity from the cell surface of the ΔSCIP Schwann cells, as well as the supernatant. The activity is associated with a high molecular weight complex that can be seen in, which is present in the fraction isolated from the mutant, but not the wt Schwann cells. This complex is observed only when the proteins are separated on native, nondenaturing gels.

References

Aguayo, A. J., Peyronnard, J. M., and. Bray, G. M. (1973). A quantitative ultrastructural study of regeneration from isolated proximal stumps of transected unmyelinated nerves. Journal of Neuropathology & Experimental Neurology 32, 256–70.

Bermingham, J. R., Jr., Scherer, S. S., O'Connell, S., Arroyo, E., Kalla, K. A., Powell, F. L., and Rosenfeld, M. G. (1996). Tst-1/Oct-6/SCIP regulates a unique step in peripheral myelination and is required for normal respiration. Genes & Development 10, 1751–62.

Bieri, P. L., Arezzo, J. C., and Weinstein, D. E. (1997). Abnormal Nerve Conduction In Mice Expressing A Targeted Amino Terminal Deletion of the POU Transcription Factor SCIP. J. Neuroscience Res. 50, 821–828.

Blight, A. R., and Young, W. (1989). Central axons in injured cat spinal cord recover electrophysiological function following remyelination by Schwann cells. Journal of the Neurological Sciences 91, 15–34.

Bray, G. M., Peyronnard, J. M., and Aguayo, A. J. (1972). Reactions of unmyelinated nerve fibers to injury. An ultrastructural study. Brain Research 42, 297–309.

Brockes, J. P., and Raff, M. C. (1979). Studies on cultured rat Schwann cells. II. Comparison with a rat Schwann cell line. In Vitro 15, 772–8.

Crawford, T. O., Hsieh, S. T., Schryer, B. L., and Glass, J. D. (1995). Prolonged axonal survival in transected nerves of C57BL/Ola mice is independent of age. Journal of Neurocytology 24, 333–40.

Easter, S. S., Jr., Ross, L. S., and Frankfurter, A. (1993). Initial tract formation in the mouse brain. Journal of Neuroscience 13, 285–99.

Faus, I., Hsu, H. J., and Fuchs, E. (1994). Oct-6: a regulator of keratinocyte gene expression in stratified squamous epithelia. Molecular & Cellular Biology 14, 3263–75.

Fawcett, J. W., and Keynes R. J. (1988). Axonal growth and Schwann cell migration into basal lamina grafts in the rat sciatic nerve. Soc. Neurosci. Abstr. 14, 164.

Feneley, M. R., Fawcett, J. W., and Keynes, R. J. (1991). The role of Schwann cells in the regeneration of peripheral nerve axons through muscle basal lamina grafts. Experimental Neurology 114, 275–85.

Friede, R. L., and Samorajski, T. (1967). Relation between the number of myelin lamellae and axon circumference in fibers of vagus and sciatic nerves of mice. Journal of Comparative Neurology 130, 223–31.

Fyodorov, D., and Deneris, E. (1996). The POU domain of SCIP/Tst-1/Oct-6 is sufficient for activation of any acetylcholine receptor promoter. Molecular & Cellular Biology 16, 5004–14.

Gilmore, S. A., and Duncan, D. (1968). On the presence of peripheral-like nervous and connective tissue within irradiated spinal cord. Anatomical Record 160, 675–90.

Glass, J. D., Brushart, T. M., George, E. B., and Griffin, J. W. (1993). Prolonged survival of transected nerve fibers in C57BL/Ola mice is an intrinsic characteristic of the axon. Journal of Neurocytology 22, 311–21.

Glass, J. D., and Griffin, J. W. (1994). Retrograde transport of radiolabeled cytoskeletal proteins in transected nerves. Journal of Neuroscience 14, 3915–21.

Griffin, J. W., George, E. B., and Chaudhry, V. (1996). Wallerian degeneration in peripheral nerve disease. Baillieres Clinical Neurology 5, 65–75.

Gulati, A. K. (1988). Evaluation of a cellular and cellular nerve grafts in repair of rat peripheral nerve. Journal of Neurosurgery 68, 117–23.

Gundersen, R. W., and Barrett, J. N. (1980). Characterization of the turning response of dorsal root neurites toward nerve growth factor. Journal of Cell Biology 87, 546–54.

Hall, S. M. (1986). Regeneration in cellular and a cellular autografts in the peripheral nervous system. Neuropathology & Applied Neurobiology 12, 27–46.

He, X., Gerrero, R., Simmons, D M, Park, R E, Lin, C J, Swanson, L W and Rosenfeld, MG. (1991). Tst-1, a member of the POU domain gene family, binds the promoter of the gene encoding the cell surface adhesion molecule P0. Mol. Cell. Biol. 11: 1739–1744 11, 1739–1744.

Hoffman, P. N., and Lasek, R. J. (1975). The slow component of axonal transport. Identification of major structural polypeptides of the axon and their generality among mammalian neurons. Journal of Cell Biology 66, 351–66.

Ide, C., Tohyama, K., Yokota, R., Nitatori, T., and Onodera, S. (1983). Schwann cell basal lamina and nerve regeneration. Brain Research 288, 61–75.

Jaegle, M., Mandemakers, W., Broos, L., Zwart, R., Karis, A., Visser, P., Grosveld, F., and Meijer, D. (1996). The POU factor Oct-6 and Schwann cell differentiation. Science 273, 507–10.

Jenq, C. B., Jenq, L. L., Bear, H. M., and Coggeshall, R. E. (1988). Conditioning lesions of peripheral nerves change regenerated axon numbers. Brain Research 457, 63–9.

Kater, S. B., Mattson, M. P., Cohan, C., and Connor, J. (1988). Calcium regulation of the neuronal growth cone. [Review] [53 refs]. Trends in Neurosciences 11, 315–21.

Le Beau, J. M., LaCorbiere, M., Powell, H. C., Ellisman, M. H., and Schubert, D. (1988). Extracellular fluid conditioned during peripheral nerve regeneration stimulates Schwann cell adhesion, migration and proliferation. Brain Research 459, 93–104.

Lemke, G., Lamar, E., and Patterson, J. (1988). Isolation and analysis of the gene encoding peripheral myelin protein zero. Neuron 1, 73–83.

Maycox, P. R., Ortuno, D., Burrola, P., Kuhn, R., Bieri, P. L., Arrezo, J. C., and Lemke, G. (1997). A transgenic mouse-model for human hereditary neuropathy with liability to pressure palsies. Molecular & Cellular Neurosciences 8, 405–16.

McQuarrie, I. G. (1985). Effect of conditioning lesion on axonal sprout formation at nodes of Ranvier. Journal of Comparative Neurology 231, 239–49.

Messing, A., Behringer; R. R., Hammmang, J. P., Palmiter, R. D., Brinster, R. L., and Lemke, G. (1992). P0 promoter directs expression of reporter and toxin genes to Schwann cells of transgenic mice. Neuron 8; 507–20.

Messing, A., Behringer, R. R., Wrabetz, L., Hammang, J. P., Lemke, G., Palmiter, R. D., and Brinster, R. L. (1994). Hypomyelinating peripheral neuropathies and schwannomas in transgenic mice expressing SV40 T-antigen. Journal of Neuroscience 14, 3533–9.

Monuki, E. S., Kuhn, R., and Lemke, G. (1993). Repression of the myelin P0 gene by the POU transcription factor SCIP. Mechanisms of Development 42, 15–32.

Morrissey, T. K., Levi, A. D., Nuijens, A., Sliwkowski, M. X., and Bunge, R. P. (1995). Axon-induced mitogenesis of human Schwann cells involves heregulin and p185erbB2.

nomena in chronic experimental allergic encephalomyelitis. Journal of Neuropatholgy & Experimental Neurology 34, 209–21.

Suzuki, N., Rohdewohid, H., Neuman, T., Gruss, P., and Scholer, H. R. (1990). Oct-6: a POU transcription factor expressed in embryonal stem cells and in the developing brain. EMBO Journal 9, 3723–32.

Tobler, A., Schreiber, E., and Fontana, A. (1993). The human Oct-6 POU transcription factor lacks the first 50 amino acids of its murine counterpart. Nucleic Acids Research 21, 1043.

Walter, J., Allsopp, T. E., and Bonhoeffer, F. (1990). A common denominator of growth cone guidance and collapse? Trends in Neurosciences 13, 447–52.

Weinstein, D. E., Burrola, P. G., and Lemke, G. (1995). Premature Schwann cell differentiation and hypermyelination in mice expressing a targeted antagonist of the POU transcription factor SCIP. Molecular & Cellular Neurosciences 6,212–29.

Zorick, T. S., Syroid, D. E., Arroyo, E., Scherer, S. S., Lemke, G. (1996). The transcription factors SCIP and Krox-20 mark distinct stages and cell fates in Schwann cell differention. Mol. and Cell. Neurosci. 8, 129–145.

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
cgctctctcc accccacaga c                                              21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
gccgcctccc gccgccagca t                                              21
```

Proceedings of the National Academy of Sciences of the United States of America 92, 1431–5.

Scaravilli, F., Love, S., and Myers, R. (1986). X-irradiation impairs regeneration of peripheral nerve across a gap. Journal of Neurocytology 15, 439–49.

Scherer, S. S., Wang, D. Y., Kuhn, R., Lemke, G., Wrabetz, L., and Kamholz, J. (1994). Axons regulate Schwann cell expression of the POU transcription factor SCIP. Journal of Neuroscience 14, 1930–42.

Snyder, D. H., Valsamis, M. P., Stone, S. H., and Raine, C. S. (1975). Progressive demyelination and reparative phe-

What is claimed is:

1. A method of culturing nervous tissue that comprises axons, the method comprising contacting said tissue in culture with an effective amount of Schwann cells expressing ΔSCIP under the control of a Schwann cell-specific $P_0$ promoter to induce axonal growth in said nervous tissue, wherein the ΔSCIP is a mammalian SCIP with a deleted amino terminus, an intact POU domain, and is able to induce overexpression of myelin structural genes.

* * * * *